United States Patent [19]

Yau

[11] Patent Number: 4,972,701
[45] Date of Patent: Nov. 27, 1990

[54] OSMOTIC METHOD FOR DETERMINING THE MOLECULAR WEIGHT OF SOLUTES IN SOLUTION WITH A SOLVENT

[75] Inventor: Wallace W. Yau, Newark, Del.

[73] Assignee: E. I. du Pont de Nemours and Company, Wilmington, Del.

[21] Appl. No.: 400,406

[22] Filed: Aug. 31, 1989

[51] Int. Cl.⁵ ............................................. G01N 30/00
[52] U.S. Cl. .................................. 73/61.1 C; 73/64.3
[58] Field of Search ............................ 73/64.3, 61.1 C

[56] References Cited

U.S. PATENT DOCUMENTS

| | | | |
|---|---|---|---|
| 4,505,149 | 3/1985 | Trumbore | 73/61.1 C X |
| 4,627,271 | 12/1986 | Abbott et al. | 73/61.1 C X |
| 4,775,943 | 10/1988 | Chamberlin et al. | 73/61.1 C X |
| 4,876,882 | 10/1989 | Yau | 73/61.1 C X |

OTHER PUBLICATIONS

Billmeyer, Textbook of Polymer Science, Third Edition, John Wiley & Sons, pp. 186–197 (1984).
Ouano, A. *Gel Permeation Chromatography VII–Molecular Weight* in Journ. of Poly. Sci. No. 43, pp. 299–310, 1973.

*Primary Examiner*—Hezron E. Williams
*Assistant Examiner*—Joseph W. Roskos

[57] ABSTRACT

There is disclosed apparatus and method for determining molecular weight by osmometry. A fluid circuit is used having two pressure measurement zones, one responsive only to viscosity effects and the other to both viscosity and osmotic effects. The osmotic effects are caused by cross-linked polymeric material within one zone capable of expanding and contracting in response to the presence of a solvent and a solution, respectively, thereby changing the effective radius of the zone and hence the pressure.

8 Claims, 11 Drawing Sheets

OSMOTIC METHOD FOR DETERMINING THE MOLECULAR WEIGHT OF SOLUTES IN SOLUTION WITH A SOLVENT

TECHNICAL FIELD

The present invention relates to a novel osmometer having high sensitivity and short equilibration time. This osmometer can be used as an on-line gel permeation chromatography (GPC) detector for absolute molecular weight determination.

BACKGROUND

Osmometry is one of the few absolute molecular weight techniques used in the characterization of polymers. In the case of membrane osmometry, a semipermeable membrane can be used to separate a polymer solution from its solvent phase. The difference in chemical potential between the solution and the solvent causes the solvent to diffuse through the semipermeable membrane to the solution side of the membrane, until a static pressure difference, the so-called osmotic pressure, is established to counter-balance the chemical potential difference. The magnitude of the osmotic pressure is proportional to the number of polymer molecules present in the solution, and, therefore, provides a measure of the number-average molecular weight of the polymer. Most commercially available osmometers involve difficult measurements and long periods of time to reach osmotic equilibrium.

SUMMARY OF THE INVENTION

The novel osmometer of the present invention can be used to measure number average molecular weight of polymers and other solutes (as well as molecular weight of solutes of monodispersed molecular weight) by making use of an osmotic effect occurring in a tube or other fluid zone across which a pressure drop can be measured. The osmotic effect can be caused by placing within the tubing or zone gel particles (or other means) which can expand in the presence of the solvent and which subsequently can contract in the presence of a sample solution of the solvent and the solute, the gel (or other means) being at least partially impenetrable to the solute. The presence of the solute particles in the sample solution exterior to the gel particles, which gel particles have previously absorbed solvent, causes a difference in chemical potential across the interface separating the interior of the gel particles and the solution, thereby causing solvent to leave the gel and enter the solution side of the interface. The result of this migration of solvent is to cause the gel (or other means) to shrink, thereby reducing the flow resistance caused by the gel to the flowing solution (or solvent) within the tube or zone. Very small sized gel particles can be used, thereby leading to very short equilibration times.

BRIEF DESCRIPTION OF THE DRAWING

The Drawing consists of eleven figures, of which

DETAILED DESCRIPTION OF THE INVENTION

The invention can be better understood with reference to the Drawing, wherein like elements are represented by like reference numerals.

Figure 1:
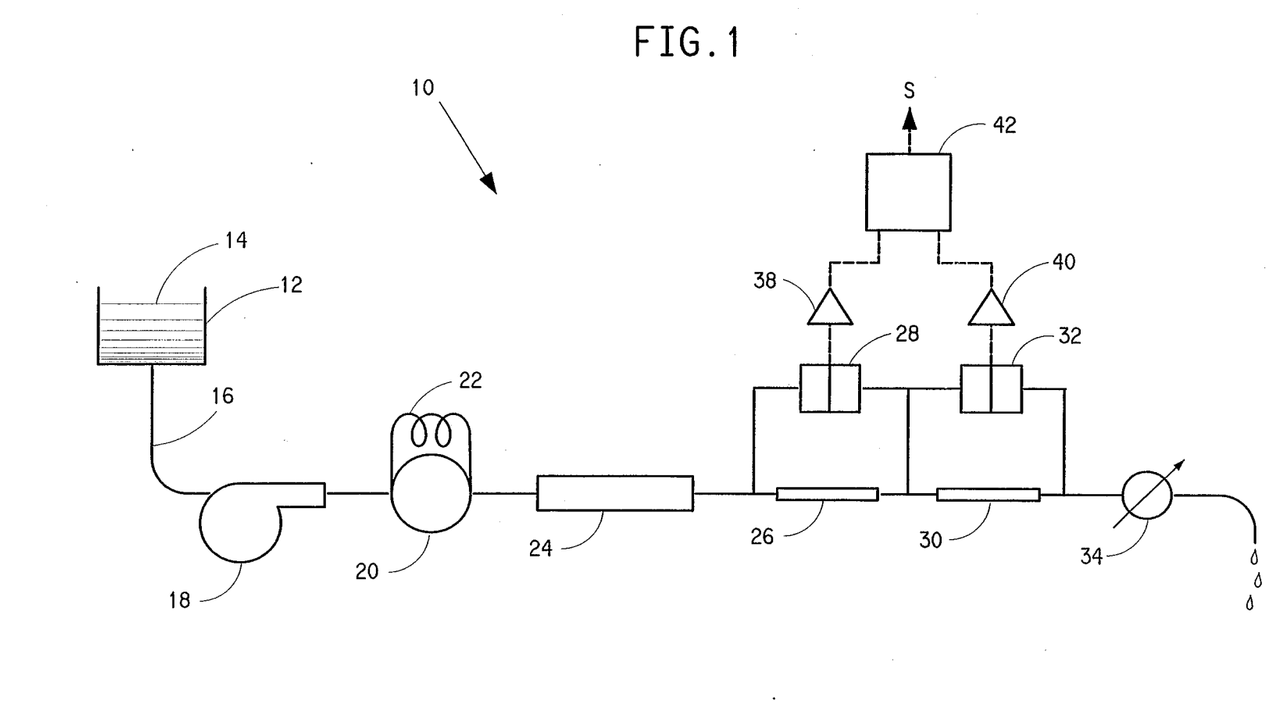
FIG. 1 shows apparatus in accordance with the present invention.

Referring now to FIG. 1, there is seen an apparatus 10 in accordance with the present invention. A reservoir 12 contains a solvent 14. Tubing 16 connects the reservoir 12 to a pump 18 which pumps the solvent 14 to an injection valve 20, which can be used either to pass the solvent 14 directly downstream or to introduce a sample solution (not shown) comprising a solute whose molecular weight is to be determined and the solvent into the flowing solvent 14 as a substantially localized volume within the stream. Conveniently, the sample solution can be introduced from a sample loop 22 of predetermined volume as a substantially localized volume within the flowing solvent 14. The stream of solvent 14, now containing the sample as a substantially localized volume can enter an optional gel permeation column 24 which can be used to separate solute components on the basis of their molecular size. The flowing stream of solvent 14, containing the substantially localized volume of sample solution, next enters a first measurement zone 26 across which a pressure transducer 28 can be used to measure the pressure drop $\Delta P$ occurring across the zone 26. Next, the flowing stream of solvent 14, containing the substantially localized volume of sample solution, enters a second measurement zone 30 across which a pressure transducer 32 can be used to measure the pressure drop $\Delta P$ occurring across the second zone. It should be emphasized that there is no fluid flow through transducers 28 and 32. Suitable pressure transducers are the well-known diaphragm types such as those manufactured by Celesco Transducer Products, Inc. (Conestoga Park, Calif.). Typically, each transducer 28, 32 is connected across its respective measurement zone by "T" connectors (not shown). Finally, the flowing stream of solvent 14, containing the substantially localized volume of solution, enters a concentration detector 34 such as a UV or refractive index detector. The detector 34 can be placed anywhere in the fluid circuit downstream of the column 24. It should be emphasized that in batch-mode operations, the detector 34 can be omitted if the concentration of the solute in the sample loop 22 is known. Finally, the flowing stream of solvent 14 can be emptied into an appropriate waste container (not shown).

Typically, first measurement zone 26 and second measurement zone 30 comprise tubes of small inside diameter, such as microbore tubes. Typically, the inside diameter of these tubes is in the range of $10^{-2}$ to $10^{-1}$ inches.

Either the first measurement zone 26 or second measurement zone 30 contains means for absorbing the solvent and expanding to a first volume and releasing the solvent in response to the presence of the sample solution of the solute and the solvent and contracting to a smaller second volume. Suitable means include cross-linked polymeric packing materials having a pore size less than about 50 angstroms. It is important that the polymeric packing material have a molecular weight cut-off such that at least a portion of the solute material will not penetrate into the interior of the packing material. This is important in order to produce an osmotic effect between the solution outside the packing material and the solvent inside the packing material.

Figure 2:
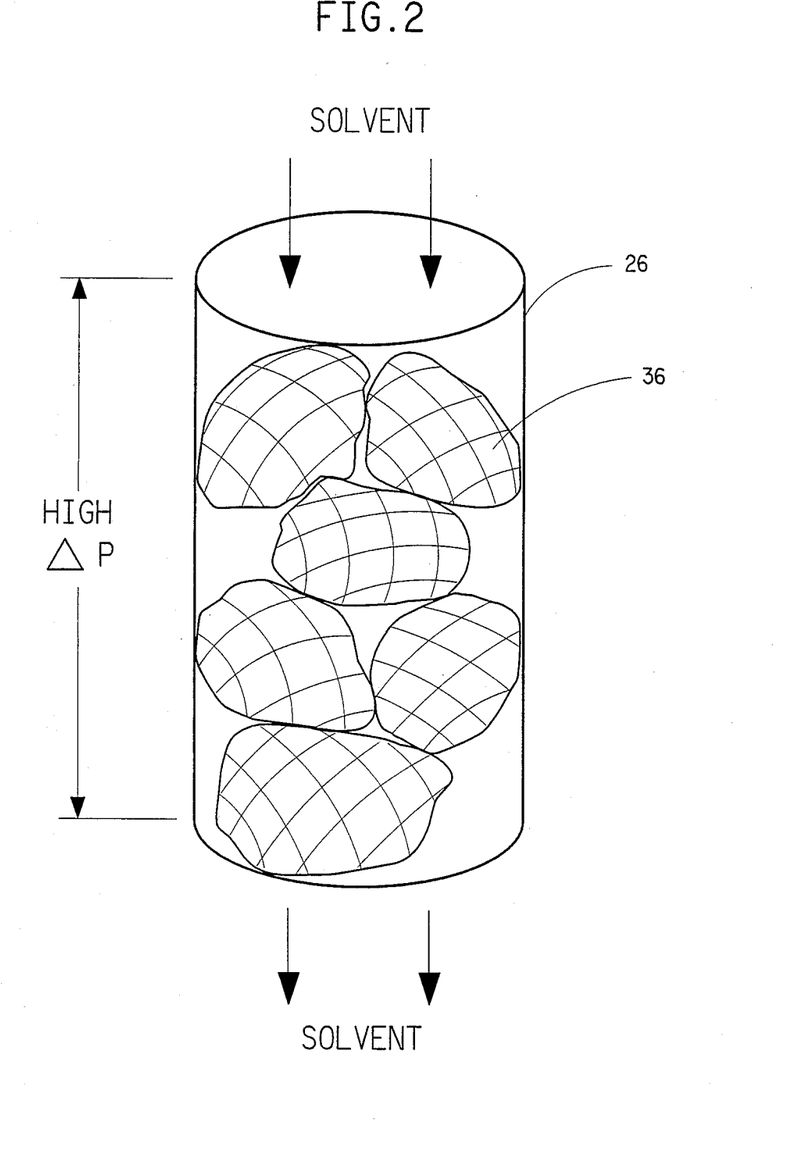
FIG. 2 shows a pressure measurement zone containing means for absorbing the solvent, which means have expanded to a first volume $V_{1,0}$.

Referring now to FIG. 2, there is seen first measurement zone 26 showing means 36 for absorbing the solvent and expanding to a first volume and releasing the solvent in response to the presence of the sample solution and contracting to a smaller second volume. The particular means illustrated in FIG. 2 is a cross-linked polymeric material such as cross-linked polystyrene. Suitable means 36 includes, but is not limited to, gels such as Pharmacia®, Lipophilic Sephadex®, LH-2 and LH-60 and Bio-Rad®, Bio-Beads S-X1 and S-X3. As solvent enters the interior of first measurement zone 26, the means 36 absorbs the solvent and expands to an initial volume $V_{1,0}$. The expansion of the means to volume $V_{1,0}$ causes increased flow resistance to solvent 14, thereby resulting in an initial pressure difference $\Delta P$ across the first measurement zone 26.

Figure 3:
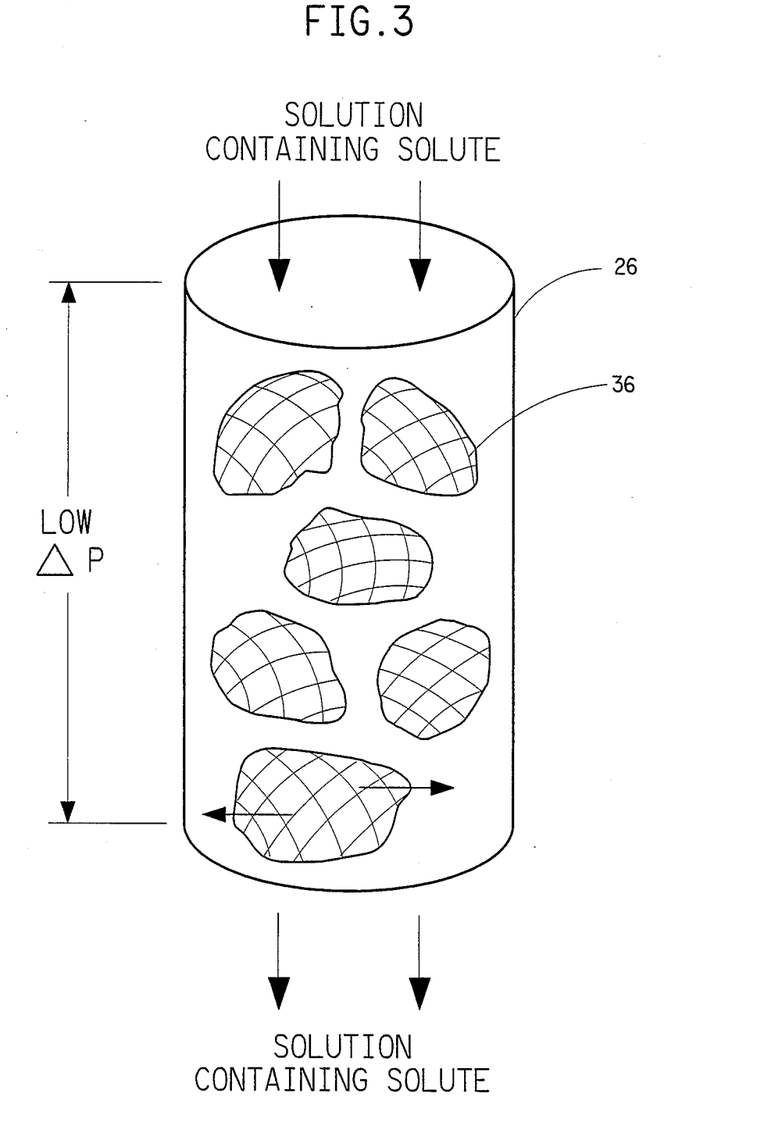
FIG. 3 shows the pressure measurement zone of FIG. 2 in which the means has been exposed to solute, causing the means to contract to volume $V_{1,S}$.

Referring now to FIG. 3, there is seen first measurement zone 26 as the substantially localized volume of sample solution containing solute passes through zone 26. It can be seen that the means 36 has released previously absorbed solvent 14 in response to the presence of the solution. By releasing the solvent, the means 36 has contracted to a smaller volume $V_{1,S}$, thereby decreasing the flow resistance across tube 26. This, in turn, leads to a lower pressure difference $\Delta P$ across the first measurement zone 26.

It should be emphasized that either the first measurement zone 26 or the second measurement zone 30 can be used to contain the means 36. The pressure drop $\Delta P$ across a measurement zone containing the means 36 will reflect not only the resistance to fluid flow caused by the expanded or contracted means 36, but also an effect attributable to the viscosity of the solution or solvent, depending upon which is passing through at any particular time.

Referring again to FIG. 1, it can be seen that there are two measurement zones 26 and 30, in fluid communication with each other, only one of which contains the means 36. Consequently, in that zone which does not contain means 36 the pressure difference $\Delta P$ will be a function of viscosity, while in the measurement zone which contains means 36, the pressure difference $\Delta P$ will be a function not only of viscosity, but also of osmotic effects.

Each pressure transducer 28, 32 is connected to an amplifier 38, 40 whose outputs are fed into a differential log amplifier 42. The output T of each transducer/amplifier can be expressed as $$T = g \cdot \Delta P$$

where g represents the amplifier gain and $\Delta P$ represents the pressure drop across the measurement zone. The output of the differential log amplifier can then be represented as $$S = \ln\left(\frac{g'\Delta P'}{g\Delta P}\right)$$

where the primed and unprimed quantities refer generally to the two measurement zones 26 and 30. Suitable amplifiers 38 and 40 include Texas Instruments TL083ACN dual operational amplifier, and a suitable log amplifier includes a Burr Brown Log 100 JP.

Figure 4:
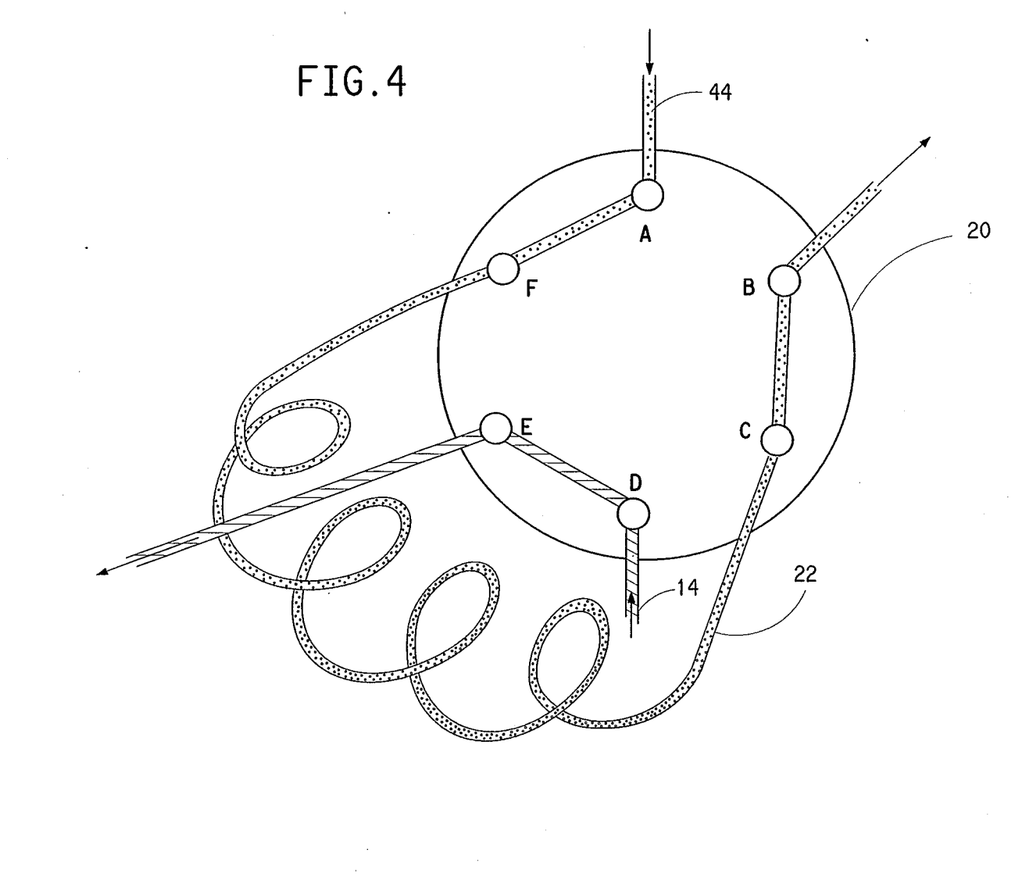
FIG. 4 shows a sample injection valve in the "load" position
Figure 5:
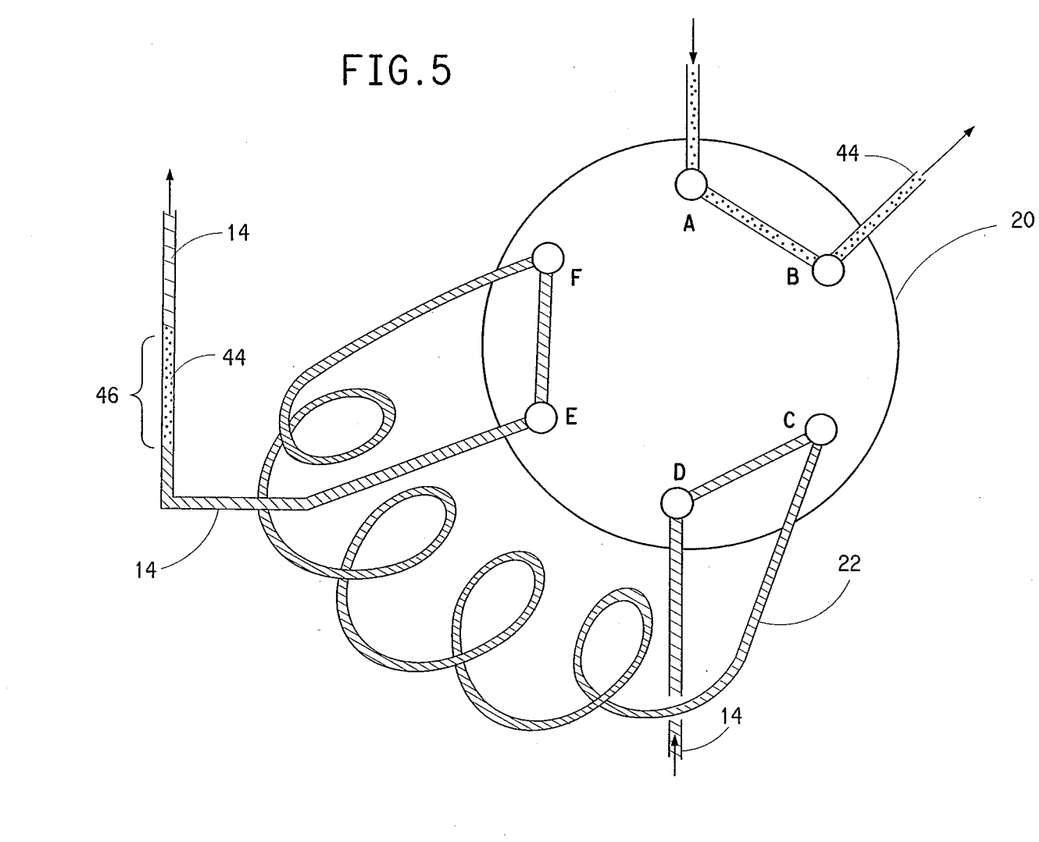
FIG. 5 shows the sample injection valve of FIG. 4 in the "run" position

Referring now to FIGS. 4 and 5 there is seen in greater detail the sample injection valve 20 which can be, for example, a 2-position, 6-port valve such as the CV6UHPA valve sold by Valco Instruments, Inc. (Houston, Tex.).

FIG. 4 represents the valve 20 in the "load" position. The solvent 14 (represented by the crosshatched areas) enters the port designated "D" and exits the port designated "E" to allow for continuous flow of solvent 14 through apparatus 10. The sample 44 (a solution of solute and solvent 14, represented by the shaded area) is injected into sample loop 22 at the port designated "A". Conveniently, the sample 44 can be loaded using a hypodermic syringe. The sample 44 flows from port "A" through port "F" and fills sample loop 22, enters the valve through port "C" and flows out of the valve 20 through port "B" into, for example, a waste container.

FIG. 5 represents the valve 20 in the "run" position. The sample 44 still enters the valve 20 at port "A", but now directly exits at port "B". The previously introduced sample, shown in FIG. 4, is pushed out of sample loop 22 by solvent 14, which still enters valve 20 at port "D", but which in the "run" mode is diverted from port "D" to port "C" where it flows out of the valve 20 through ports "F" and ultimately port "E". The sample 44 can be seen as a substantially localized volume 46 indicated by the bracket. It can be seen that substantially localized volume 46 of sample 44 is bordered on either side by solvent 14.

The manner in which the osmometer in accordance with the present invention operates can, perhaps, be best understood with reference to the following mathematical relationships. In the description which follows, the measurement zone which contains the means 36 is referred to as the "analytical" zone denoted in the mathematical formulas by the subscript "A", and the measurement zone not containing the means 36 is referred to as the "reference" zone denoted by the subscript "R". The subscript "0" denotes the condition when solvent only is flowing through a measurement zone, and the subscript "S" denotes the condition when sample solution is flowing through a measurement zone.

In general, the pressure drop $\Delta P$ across a tube of length L and radius r caused by the flow therethrough of a fluid of viscosity $\eta$ can be expressed by Poiseuille's Law as follows:

$$\Delta P = \frac{8QL\eta}{\pi r^4} \quad (1)$$

where Q is the volumetric flow rate, and $\pi$ is the numerical constant 3.1416.

In the case of a pressure transducer connected to an amplifier providing a gain g, the output voltage signal T can be expressed as follows:

$$T = \frac{g8QL\eta}{\pi r^4} \quad (2)$$

In the present invention, both the analytical zone and reference zone experience pressure drops $\Delta P$ as follows:

$$\Delta P_R = \frac{8QL_R\eta}{\pi r_R^4}, \; \Delta P_A = \frac{8QL_A\eta}{\pi r_A^4} \quad (3)$$

When converted to voltage output signals by amplifiers 38, 40, the pressure drops can be expressed as follows:

$$T_R = \frac{g_R 8QL_R\eta}{\pi r_R^4}, \; T_A = \frac{g_A 8QL_A\eta}{\pi r_A^4} \quad (4)$$

When the signals $T_R$ and $T_A$ are processed by differential log amplifier 42, the output of such log amplifier can be expressed generally as follows:

$$S = \ln\left(\frac{T_R}{T_A}\right) \quad (5)$$

It should be emphasized that the value $r_A$ is the effective radius of a tube—not containing means 36—whose radius is such as to provide a pressure drop equal to that of the measurement zone containing means 36.

When only solvent 14 is flowing across the reference and analytical zones, the signal from the differential log amplifier can be expressed specifically as follows:

$$S_0 = \ln\left(\frac{g_R L_R}{r_R^4} \cdot \frac{r_{A,0}^4}{g_A L_A}\right) \quad (6)$$

where $r_{A,0}$ is the effective radius of a tube not containing means 36, whose radius is such as to provide a pressure drop $\Delta P$ equal to that across the analytical zone when the means 36 is expanded to its first volume $V_{1,0}$.

When sample solution 44 is flowing across the reference and analytical zones, the signals from the differential log amplifier can be expressed specifically as follows:

$$S_S = \ln\left(\frac{g_R L_R}{r_R^4} \cdot \frac{r_{A,S}^4}{g_A L_A}\right) \quad (7)$$

where $r_{A,S}$ is the effective radius of a tube not containing means 36, whose radius is such as to provide a pressure drop $\Delta P$ equal to that across the analytical zone when the means 36 is contracted to its smaller volume $V_{1,S}$.

The net signal due to osmotic effects, $\Delta S$, can be expressed as follows:

$$\Delta S = S_S - S_0 = \ln\left(\frac{g_R L_R}{r_R^4} \cdot \frac{r_{A,S}^4}{g_A L_A}\right) - \ln\left(\frac{g_R L_R}{r_R^4} \cdot \frac{r_{A,0}^4}{g_A L_A}\right) \quad (8)$$

$$\Delta S = \ln\left(\frac{r_{A,S}^4}{r_{A,0}^4}\right)$$

$$\Delta S = 4\ln\left(\frac{r_{A,S}}{r_{A,0}}\right)$$

In general, the extent to which the effective radius, $r_A$, expands in response to osmotic pressure $\pi$ is a very complex phenomenon. Empirical calibration of the apparatus 10 is highly recommended by using a series of commercial polymer standards of known molecular weights. Nevertheless, the following simple theory is offered to explain the observed osmotic effect.

The means 36 (typically gel particles) in a tightly packed bed are somewhat restricted in their ability to expand due to the geometrical confinement imposed by neighboring particles. Particle volume expansion is only possible by extruding into the interstitial volumes between particles. Therefore, the compressibility of the gel particle is no longer a constant, but becomes a function of pressure:

$$\frac{dV}{dP} = E, \text{ for isolated gel particle} \quad (9)$$

$$\frac{dV}{dP} = E(1 + kP), \text{ for particles in packed bed} \quad (10)$$

where
V = volume of gel particles
P = pressure
E = compressibility of the particles
k = coefficient to the pressure dependency of E.

Equation 10 is a differential equation, subject to the boundary condition of $V_1 = V_{1,0}$ at $P = P_O$, where $V_1$ represents gel particle volume generally, $P_0$ is the static pressure existing inside the packed gel column in presence of solvent 14 and $V_{1,0}$ is the volume of gel particles in presence of solvent 14. $V_1 = V_{1,S}$ at $p = P_{O-\pi}$, where $V_{1,S}$ is the volume of means 36 in the presence of sample solution 44 and $\pi$ is the osmotic pressure. Solving Equation 10 subject to these boundary conditions, we get $$V_{1,0} - V_{1,S} = E\pi + \frac{k}{2}[P_0^2 - (P_0 - \pi)^2]. \quad (11)$$

Since the volume shrinkage of gel particles in Equation (11) means a volume expansion of void space between the particles:

$$V_{2,S} = V_{2,0} + E\pi + \frac{k}{2}[P_0^2 - (P_0 - \pi)^2] \quad (12)$$

or,

-continued
$$\frac{V_{2,S}}{V_{2,0}} = 1 + \frac{E}{V_{2,0}}\pi + \frac{k}{2V_{2,0}}(\pi)(2P_0 - \pi) \quad (13)$$

where $V_2$ represents void volume generally, $V_{2,0}$ and $V_{2,S}$ are the void volumes between the particles in the presence of solvent 14 and sample solution 44, respectively.

Assuming that $$\frac{V_{2,S}}{V_{2,0}} = \left(\frac{r_{A,S}}{r_{A,0}}\right)^3 \quad (14)$$

Equation (13) becomes:

$$\left(\frac{r_{A,S}}{r_{A,0}}\right)^3 - 1 = \left(\frac{E + kP_o}{V_{2,0}}\right)\pi\left[1 - \frac{k}{2(E + kP_o)} \cdot \pi\right] \quad (15)$$

Since from Equation (8):

$$\frac{r_{A,S}}{r_{A,0}} = e^{\Delta S/4} \quad (16)$$

We have for the left side of Equation (15):

$$\left(\frac{r_{A,S}}{r_{A,0}}\right)^3 - 1 = e^{3\Delta S/4} - 1 \approx \frac{3\Delta S}{4}, \text{ for } \Delta S < 0.1 \quad (17)$$

In general, the number average molecular weight of a solute can be related to osmotic pressure and concentration as follows:

$$\frac{\pi}{C} = \frac{RT}{M_n} \quad (18)$$

where C is sample concentration, R is gas constant, T here is absolute temperature in degree Kelvin, and $M_n$ is number average molecular weight. With the insertion of Equation (17) and (18), Equation (15) becomes:

$$\frac{3\Delta S}{4} = \left(\frac{RT(E + kP_o)}{V_{2,0}}\right)\frac{C}{M_n}\left[1 - \frac{kRT}{2(E + kP_o)}\frac{C}{M_n}\right]$$

or, $$\frac{\Delta S}{C} = \frac{k_1}{M_n}(1 - k_2 C/M_n) \quad (19)$$

where $k_1 = 4RT(E + kP_o)/3V_{2,0}$, and $k_2 = kRT/2(E + kP_o)$

Since Equation (19) reflects only an approximate theory of operation of the present apparatus, the above expressions for $k_1$ and $k_2$ are not significant. Instead, one must use experimental data from polymer samples of known molecular weight values to determine $k_1$ and $k_2$. $\Delta S$ and C are both measured quantities, (C can be calculated during sample preparation, rather than measured using detector 34). Hence, $M_n$ can be calculated from Equation (19).

Figure 6A:
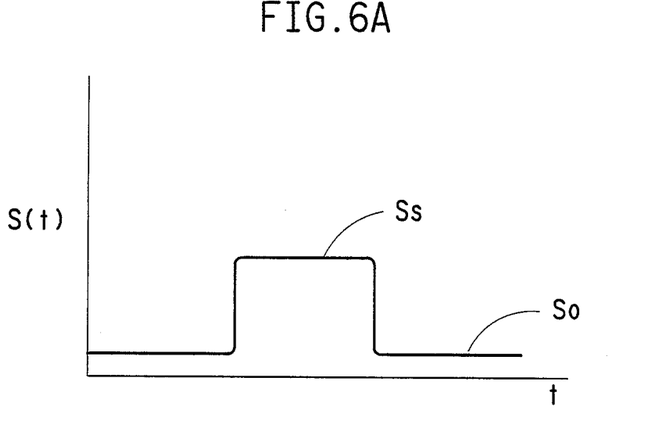
FIG. 6 shows stylized plots of S(t) and C(t) versus time for the apparatus used in a batch mode.
Figure 6B:
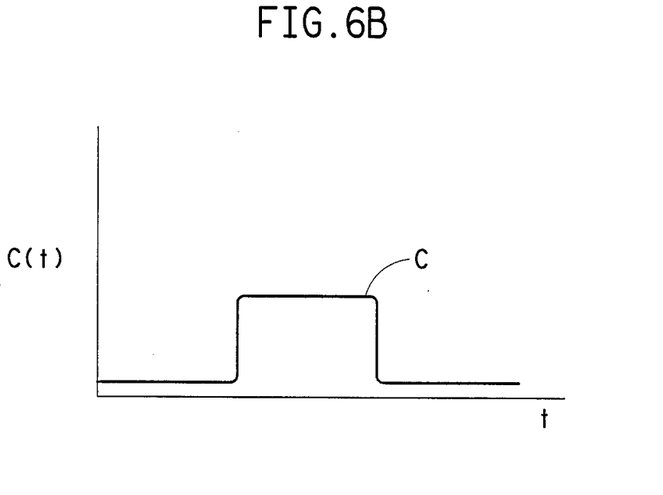

Referring now to FIG. 6, there is shown a graph of S(t) versus t(time) for the present apparatus 10 run in a so-called batch mode. The difference between the baseline $S_o$ and the peak, $S_s$, is the value $\Delta S$ and the height of the peak on the C(t) versus t plot is C. $M_n$ can be determined from the $\Delta S$ calibration curve, if available. An estimate of $M_n$ may be possible by solving $M_n$ from an approximate theory, such as that expressed in Equation 19 by using the measured values of $\Delta S$ and C.

To provide accurate results in the batch mode, it is preferable to use a sample loop 22 having a volume equal to or greater than the sum of the volumes of measurement zones 26 and 30 and the volume of any tubing interconnecting these zones. This insures that pressure effects attributable to viscosity will be caused by the same liquid in both zones.

The present apparatus 10 may also be run as an online GPC detector by using a gel permeation column 24 (FIG. 1) upstream of the two measurement zones 26, 30. In this mode, it is preferable to use a sample loop 22 having a small volume and short, small volume tubing interconnecting measurement zones 26, 30.

The column 24 is packed with well-known packing material (not shown) which is capable of separating a polydispersed solute into its components based on molecular size of the components. Suitable GPC packing materials include, but are not limited to, silica-based packings such as Lichrospher Si, Lichrospher Diol, Synchropak GPC, $\mu$-Bondagel, Protein I-series, TSK-SW, Shodex Aqpak, Catsec, Zorbax® GF, Zorbax® PSM and polymeric packings such as Waters' Microstyragel, Ultrastyragel, TSK-PW, Spheron, Shodex OH-Pak, Shodex Ionpak and Paquagel. As the sample 44 (FIGS. 4 and 5) enters column 24, the solute is separated on the basis of molecular size, larger molecules being the first to elute from the column 24.

As the various solute components enter measurement zones 26, 30, each component will generate a $\Delta P$ in each zone, and each transducer 28, 32 will generate an electrical signal which will be processed by log amplifier 42. Similarly, each solute component will generate a response in concentration detector 34, which may be placed either upstream or downstream of zones 26, 30.

Figure 7A:
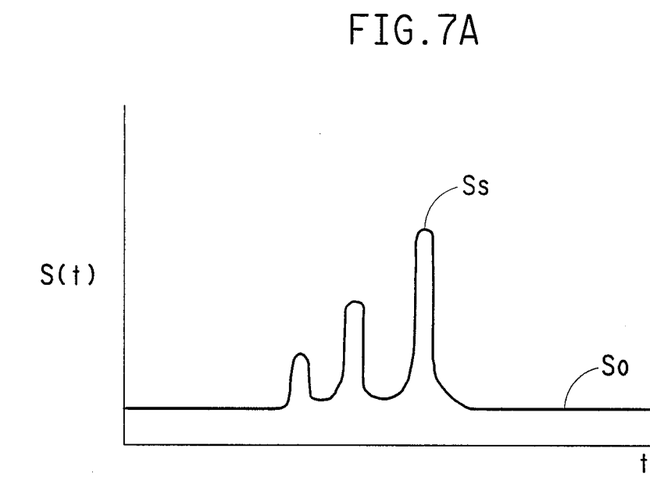
FIG. 7 shows stylized plots of S(t) and C(t) versus time for the apparatus used in a GPC mode with a three-component solute.
Figure 7B:
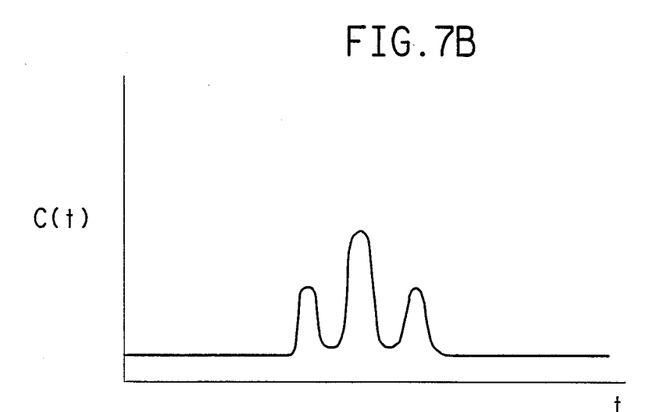

Stylized S(t) and C(t) plots for GPC-mode operation are shown in FIG. 7. The plots show a three-solute component sample separated by GPC column 24 into three separate volume fractions, each of which generated its own S(t) and C(t) peak. To calculate $M_n$ in this mode, the S(t) and C(t) curves must be correlated so that a particular point on the C(t) curve is associated with the corresponding point on the S(t) curve. It should be emphasized that in the GPC-mode, $M_n$ value of eluting solute is not a single, time-invariant value, but rather, is a function of GPC elution time. Hence, for GPC-mode operation, Equation (19) is, perhaps, better written as follows:

$$\frac{\Delta S(t)}{C(t)} = \frac{k_1}{M_n(t)}[1 - k_2 C(t)/M_n(t)] \quad (19A)$$

The present invention is illustated by the following nonlimiting examples.

EXAMPLE 1

Batch Mode

Figure 8:
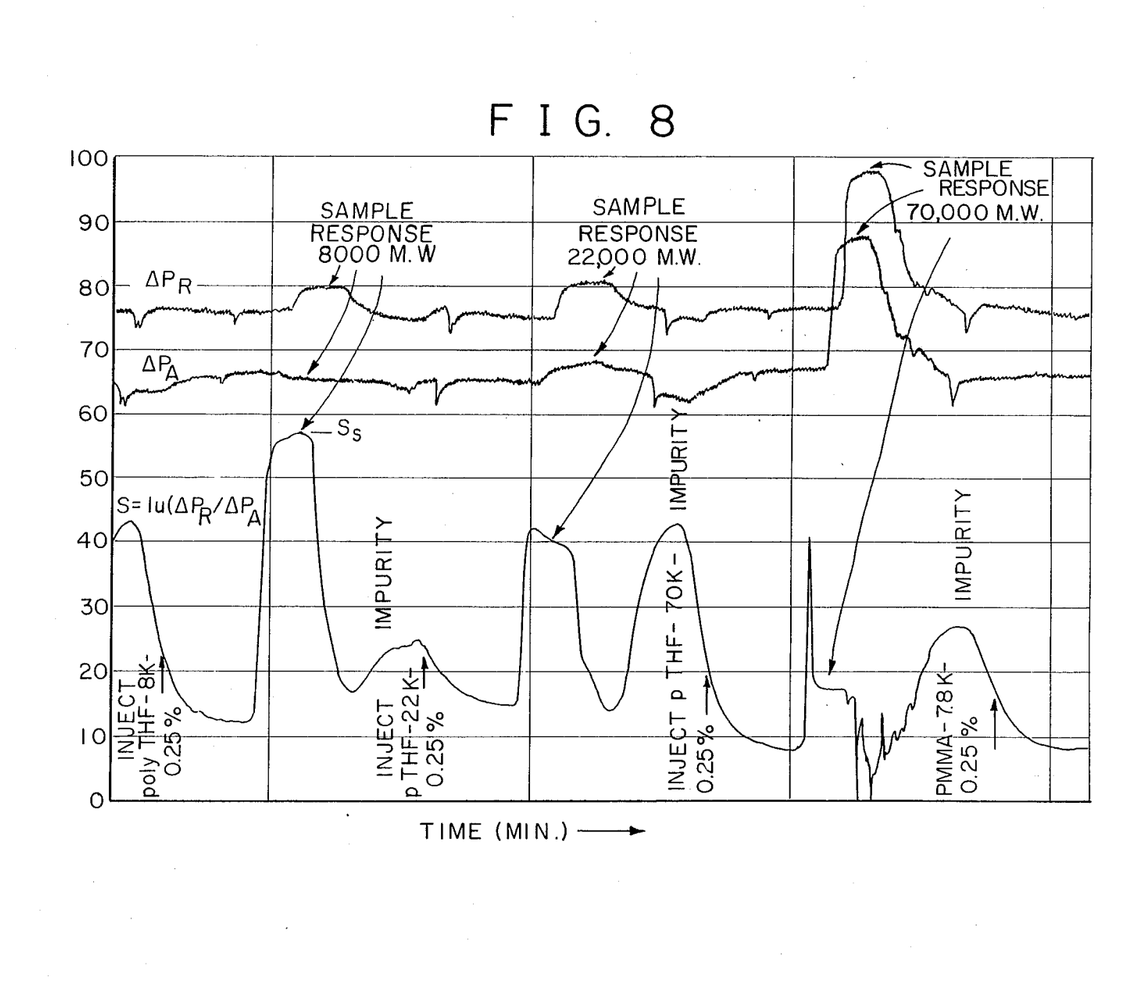
FIG. 8 shows the recorder traces for a batch osmometry experiment of three samples of polytetrahydrofuran (PTHF) of different molecular weight values.

The batch experiment results shown in FIG. 8 were obtained under the following experimental conditions (refer to the Drawing for reference numerals): LKB 2150HPLC Pump (18), Valco-CV6UHPA sample valve (20), 3 ml sample loop (22), one Ultrastyragel-40Åcolumn (24), Microbore column 50 mm×2 mm ID (26) packed with Pharmacia LH-60 lipophillic Sephadex GPC-type gel particles (36), Reference tubing of 2 in.×0.02 in. ID (30), Waters 410 refractometer (34), Celesco Transducers with 1 psi diaphragm (28, 32), pre-amplifiers TL083ACN by Texas Instrument (38, 40), Burr Brown Log 100 JP log-amplifier (42), Solvent (14) EM Science HPLC grade chloroform containing 0.85% ethanol stabilizer. A flowrate of 0.4 ml/min was used in the experiment. Sample concentration was 0.25%.

Because the stabilizer level in the chloroform solvent bought from EM Science varies somewhat from one solvent bottle to the next, an Ultrastyragel column of 40Åpore (24) was used, even though this was a batch osmometry experiment. The small pore size of this gel column serves the purpose of providing needed retention of the solvent impurity (ethanol in this case) so that the impurity responses will be separated from the sample response for more accurate measure of the sample osmotic effect. (FIG. 8 shows impurity responses well separated from the sample responses of interest). In FIG. 8, the $\Delta P_R$ trace from reference tubing (30) shows responses to pump flowrate upsets and sample viscosity effects, while the $\Delta P_A$ trace from the microgel column (26) containing gel particles (36) shows additional responses to osmotic effects attributable to the sample, causing a reduction of $\Delta P_A$ response. As shown for a low molecular weight sample (PTHF with MW=8,000), there was an actual net reduction of $\Delta P_A$ caused by osmotic effects attributable to the sample. This $\Delta P_A$ reduction clearly demonstrates for this sample that there was an appreciable osmotic effect that actually cancelled out and exceeded the sample viscosity effect on the pressure drop across the microgel column.

FIG. 8 shows that a poly-tetrahydrofuran (PTHF) standard of 8,000 molecular weight gave a $\Delta S$ value of 89 millivolts (mv) and a standard of 70,000 molecular weight gave $\Delta S$ value of 18 mv. Sample concentrations were the same, 0.25 g/dl. Substituting the data into Equation (19):

$$\frac{89}{0.25} = \frac{k_1}{8,000} (1 - 0.25 k_2/8,000) \quad (20A)$$

and $$\frac{18}{0.25} = \frac{k_1}{70,000} (1 - 0.25 k_2/70,000) \quad (20B)$$

By solving simultaneous Equations (20A) and (20B) for $k_1$ and $k_2$, one obtains $k_1 = 5.32 \times 10^6$ and $k_2 = 1.49 \times 10^4$. Therefore:

$$\frac{\Delta S}{C} = \frac{5.32 \times 10^6}{M_n} \left( 1 - 1.49 \times 10^4 \frac{C}{M_n} \right) \quad (21)$$

Equation (21) can be used to determine the $M_n$ value of other samples. For example, FIG. 8 shows the trace obtained for a PTHF sample of 0.25 g/dl concentration and a reported molecular weight value of 22,000. The $\Delta S$ value was 54 mv. By inserting $\Delta S = 54$, and $C = 0.25$ into Equation (21), one obtains a calculated $M_n$ value of 20,000 which is very close to the reported value.

Figure 9:
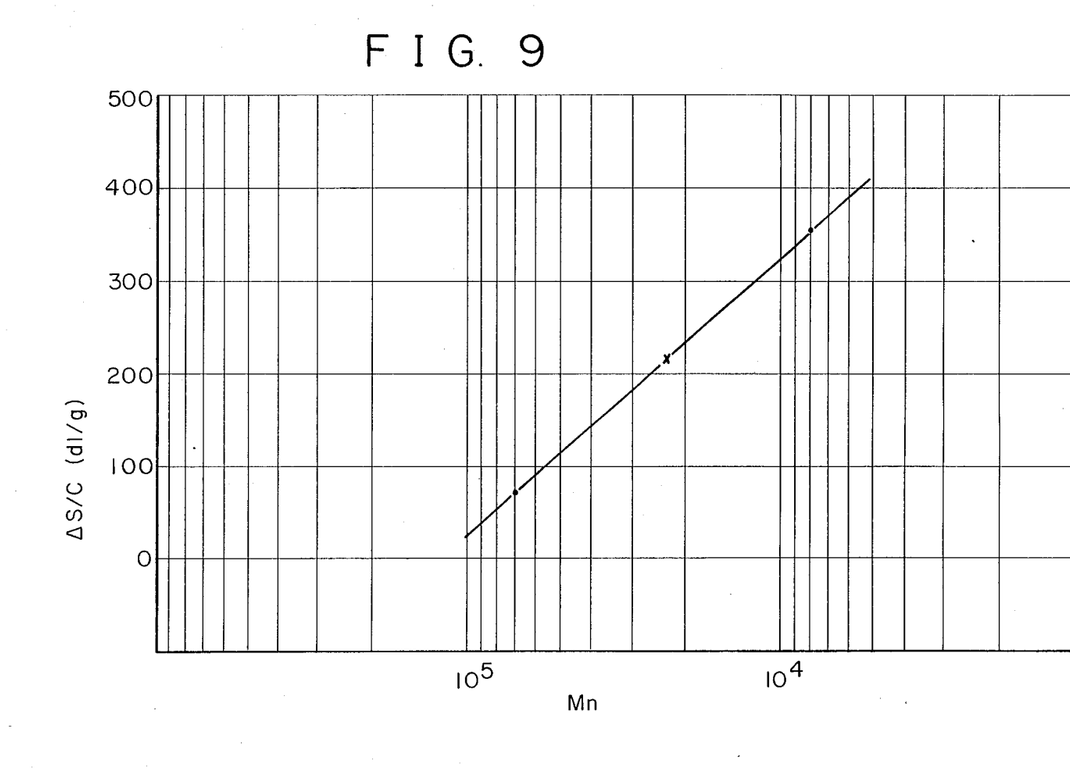
FIG. 9 shows a plot of $\Delta S/C$ versus $M_n$ for data of Example 1.

FIG. 9 shows a calibration curve for the apparatus obtained from the 70,000 and 8,000 molecular weight samples. For the 70,000 M.W. sample $\Delta S$ is 18 mV and C is 0.25 g/dl; $\Delta S/C = 72$. For the 8,000 M.W. sample $\Delta S$ is 89 mV and C is 0.25 g/dl; $\Delta S/C = 356$. The curve can be used to determine the molecular weight of the 22,000 sample as if it were an unknown. For this "unknown" $\Delta S$ is 54 mV and C is 0.25 g/dl; $\Delta S/C = 216$. Using the calibration curve, this value of $\Delta S/C$ corresponds to a molecular weight of 23,300, which is in good agreement with reported 22,000.

EXAMPLE 2

GPC-Mode

Figure 10:
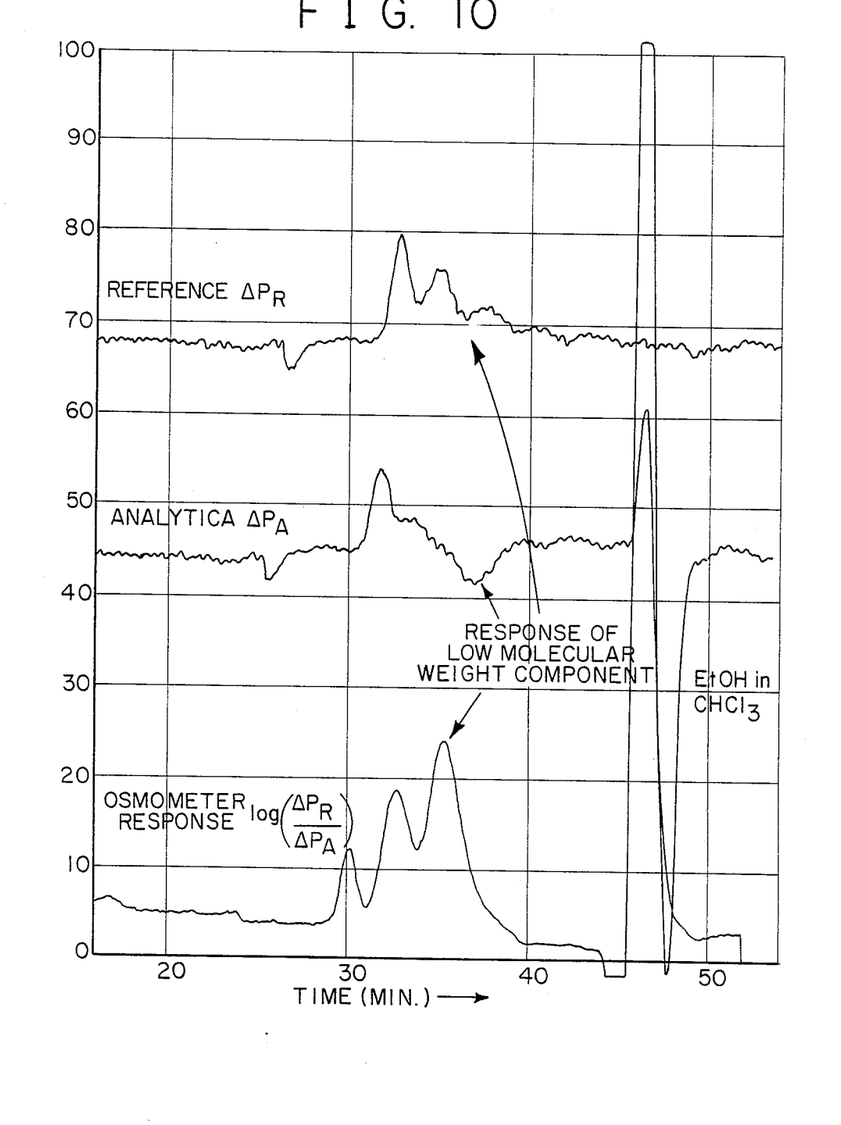
FIG. 10 shows the recorder traces for a GPC-osmometry experiment of a polymethylmethacrylate (PMMA) sample made up by a mixture of three PMMA standards of different molecular weight.
Figure 11:
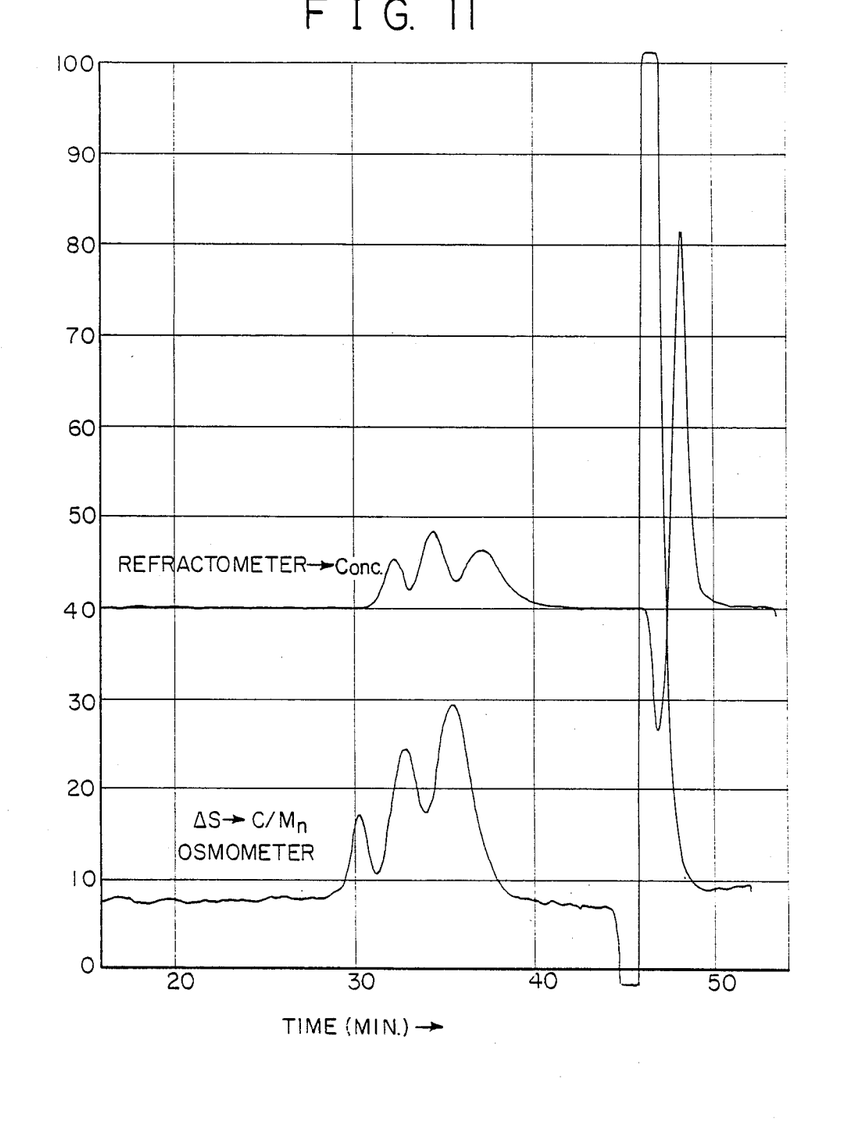
FIG. 11 shows a repeat experiment of FIG. 10 to illustrate the reproducibility of the GPC-osmometry experiment. The refractometer response is included here to show the different peak height responses as compared to the osmometer signal.

The GPC-osmometry experiments whose results are shown in FIGS. 10 and 11 were done under conditions described for the batch experiment, except for the following changes: 200 μl sample loop (22), three Du Pont PSM-bimodal GPC columns (24). A flowrate of 0.5 ml/min was used in the experiment. The sample was a 1:2:2 mixture of three PMMA standards of 79, 27.5 and 7.8 thousand molecular weight. The sample concentration was 2% total.

In the GPC results shown in FIG. 10, molecules of different sizes are separated. The late eluting low molecular weight component is shown here to have caused a small increase in $\Delta P_R$ due to the solution viscosity effect and a net decrease of the $\Delta P_A$ resulting from an osmotic effect larger than the viscosity effect for this low molecular weight species. The GPC-osmometry trace here shows the expected increase of peak heights for the lower molecular weight peaks.

The reproducibility of the GPC-osmometer response is quite good, as is shown by a repeat experiment shown in FIG. 11. (Compare the bottom two osmometer traces from the two Figures.) In the repeat experiment, a refractometer response was recorded along with the osmometer signal. The two traces shown in FIG. 11 represent the type of GPC osmometry results one would generate experimentally. Since the osmometer signal $\Delta S$ can be used to estimate the quantity $C/M_n$ at every point across the GPC elution profile, it is possible to calculate $M_n$ as a function of time by correlating $\Delta S$ with the concentration (C) information provided by the refractometer at every GPC retention volume. A plot of experimental concentration (C) values against the corresponding molecular weight ($M_n$) values, point by point across the entire GPC elution curve would therefore provide the basis to generate the desired molecular weight distribution curves for the sample.

Although the present invention has been described with respect to the specific embodiment shown in the drawing and illustrated by the previous Examples, various modifications will be suggested to those skilled in the art, making the scope of the invention limited only by the claims which follow.

What is claimed is:

1. A method for determining the number average molecular weight of a solute in solution with a solvent, comprising (1) introducing into a stream of flowing solvent a substantially localized volume of a sample comprising a solution of the solute and the solvent;

(2) passing the solvent and the sample through first and second zones in fluid communication with each other, one of said zones containing means for (1) absorbing the solvent and expanding to a first volume and (2) releasing the solvent in response to the presence of the sample and contracting to a second volume, said means being at least partially impenetrable to the solute;

(3) measuring pressure differences as functions of time across said first and second zones;

(4) determining the concentration of the solute as a function of time; and (5) relating the pressure differences and the concentration to the number average molecular weight of the solute.

2. The method of claim 1 wherein the first and second zones are microbore tubes.

3. The method of claim 2 wherein the means comprises a cross-linked polymeric material having a pore size of less than about 50 angstroms.

4. The method of claim 1 wherein after substep (1) the sample is passed through a gel permeation column, thereby separating the sample into components of different molecular weight.

5. Apparatus for determining the number-average molecular weight of a solute in solution with a solvent, comprising a source of the solvent; first means for causing said solvent to flow in a fluid circuit; second means for introducing into said fluid circuit a substantially localized volume of a sample comprising the solute in solution with the solvent; a fluid circuit comprising first and second fluid-pressure measurement zones, one of said zones containing third means for (1) absorbing the solvent and expanding to a first volume and (2) releasing the solvent in response to the presence of the sample and contracting to a second volume, said third means being at least partially impenetrable to the solute; and means for measuring the concentration of the solute.

6. Apparatus of claim 5 wherein the means for causing the solvent to flow in a fluid circuit is a pump.

7. Apparatus of claim 5 wherein the first and second fluid-pressure measurement zones are microbore tubes.

8. Apparatus of claim 7 wherein the means for (1) absorbing the solvent and expanding to a first volume and (2) releasing the solvent in response to the presence of the sample and contracting to a second volume comprises a cross-linked polymeric material having a pore size of less than about 50 angstroms.

* * * * *